(12) United States Patent
Taylor

(10) Patent No.: US 7,104,131 B2
(45) Date of Patent: Sep. 12, 2006

(54) ULTRASONIC PULSER-RECEIVER

(75) Inventor: Steven C. Taylor, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 42 days.

(21) Appl. No.: 10/803,518

(22) Filed: Mar. 17, 2004

(65) Prior Publication Data

US 2005/0204819 A1    Sep. 22, 2005

(51) Int. Cl.
G01N 29/14 (2006.01)
(52) U.S. Cl. .......................................... 73/620; 73/632
(58) Field of Classification Search ................. 73/620, 73/623, 629, 622, 632, 627
See application file for complete search history.

(56) References Cited

U.S. PATENT DOCUMENTS

| | | | | |
|---|---|---|---|---|
| 3,088,052 A | * | 4/1963 | Hickey et al. | 315/168 |
| 3,201,612 A | * | 8/1965 | Amodei | 327/302 |
| 3,566,303 A | * | 2/1971 | De Maria | 372/24 |
| 5,108,693 A | * | 4/1992 | Landry et al. | 376/245 |
| 5,303,591 A | * | 4/1994 | Dykes et al. | 73/620 |
| 5,473,934 A | * | 12/1995 | Cobb | 73/61.49 |
| 6,570,097 B1 | * | 5/2003 | Monde et al. | 174/137 B |

OTHER PUBLICATIONS

Pace, Brett W., et al., "Research & Test Reactor Fuel Elements (RTRFE)", RERTR Annual Meeting, BWX Technologies Incorporated 8 pages (Oct. 1999).
http://www.imagilent.com/pr_dpr500.html, DPR500 Product Specifications, JSR Ultrasonics, 2 pages (Oct. 4, 2003).
http://www.imagilent.com/pr_dpr300.html, DPR300 Product Specifications, JSR Ultrasonics, 2 pages (Oct. 4, 2003).
http://www.imagilent.com/pr_prc35.html, PRC35 Product Specifications, JSR Ultrasonics, 2 pages (Oct. 4, 2003).
http://www.gepower.com/dhtml/panametrics/en_us/products/pulser_receivers/index.isp/ GE Power Systems, GE Panametrics, "Pulsers-Receivers", 2 pages (Oct. 2, 2003).
http://www.gepower.com/dhtml/panametrics/en_us/products/pulser_receivers/5058pr_pulse GE Power Systems, GE Panametrics, "5058PR Pulser-Receiver", 2 pages (Oct. 2, 2003).
http://www.gepower.com/dhtml/panametrics/en_us/products/pulser_receivers/5627pr_pulse GE Power Systems, GE Panametrics, "5627RPP Remote Pulser Preamplifier", 1 page (Oct. 2, 2003).
http://www.gepower.com/dhtml/panametrics/en_us/products/pulser_receivers/preamplifiers GE Power Systems, GE Panametrics, "Preamplifiers", 2 pages (Oct. 2, 2003).

* cited by examiner

Primary Examiner—Daniel S. Larkin
Assistant Examiner—Jacques Saint-Surin
(74) Attorney, Agent, or Firm—Wells St. John, P.S.

(57) ABSTRACT

Ultrasonic pulser-receiver circuitry, for use with an ultrasonic transducer, the circuitry comprising a circuit board; ultrasonic pulser circuitry supported by the circuit board and configured to be coupled to an ultrasonic transducer and to cause the ultrasonic transducer to emit an ultrasonic output pulse; receiver circuitry supported by the circuit board, coupled to the pulser circuitry, including protection circuitry configured to protect against the ultrasonic pulse and including amplifier circuitry configured to amplify an echo, received back by the transducer, of the output pulse; and a connector configured to couple the ultrasonic transducer directly to the circuit board, to the pulser circuitry and receiver circuitry, wherein impedance mismatches that would result if the transducer was coupled to the circuit board via a cable can be avoided.

42 Claims, 4 Drawing Sheets

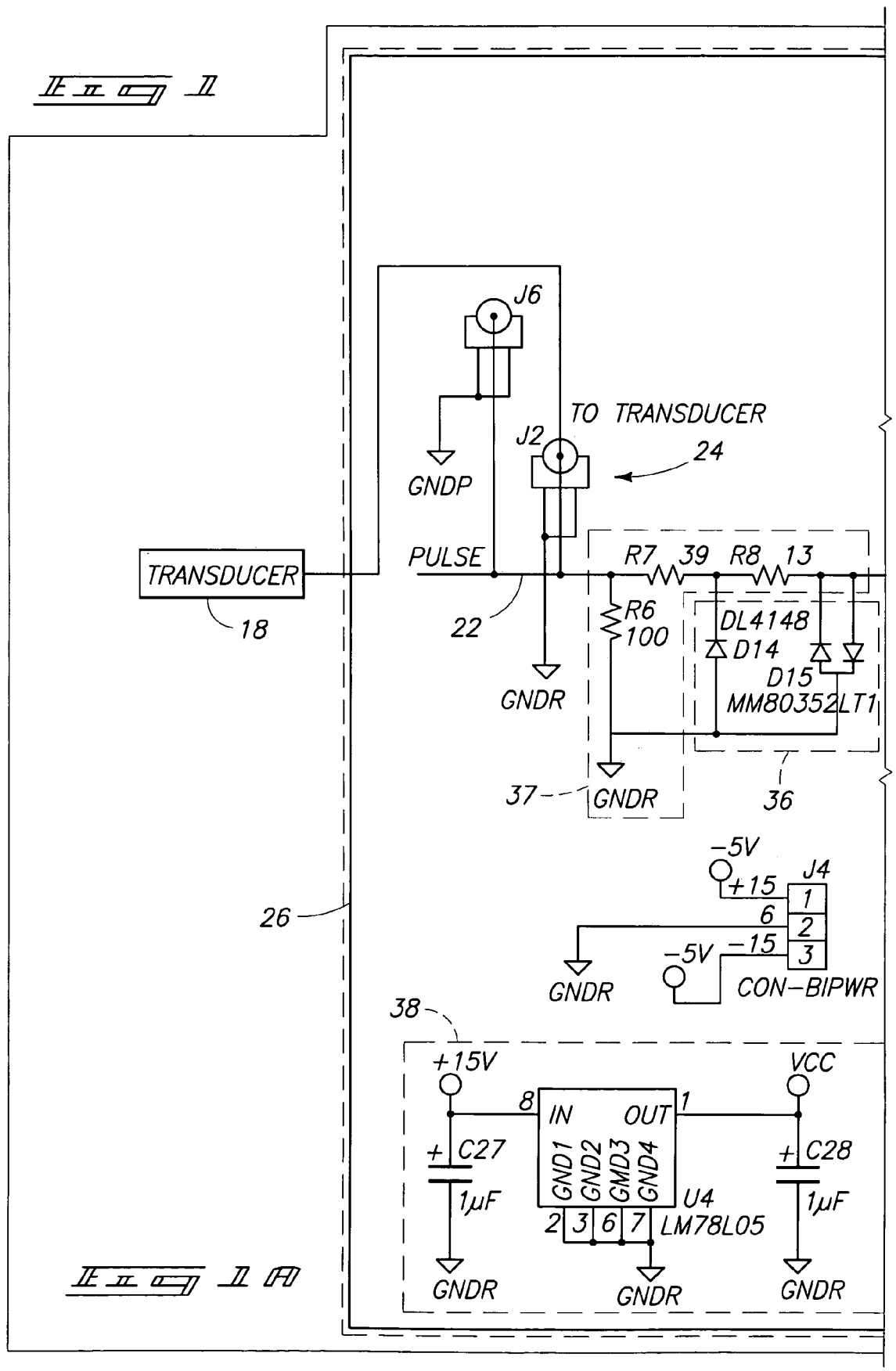

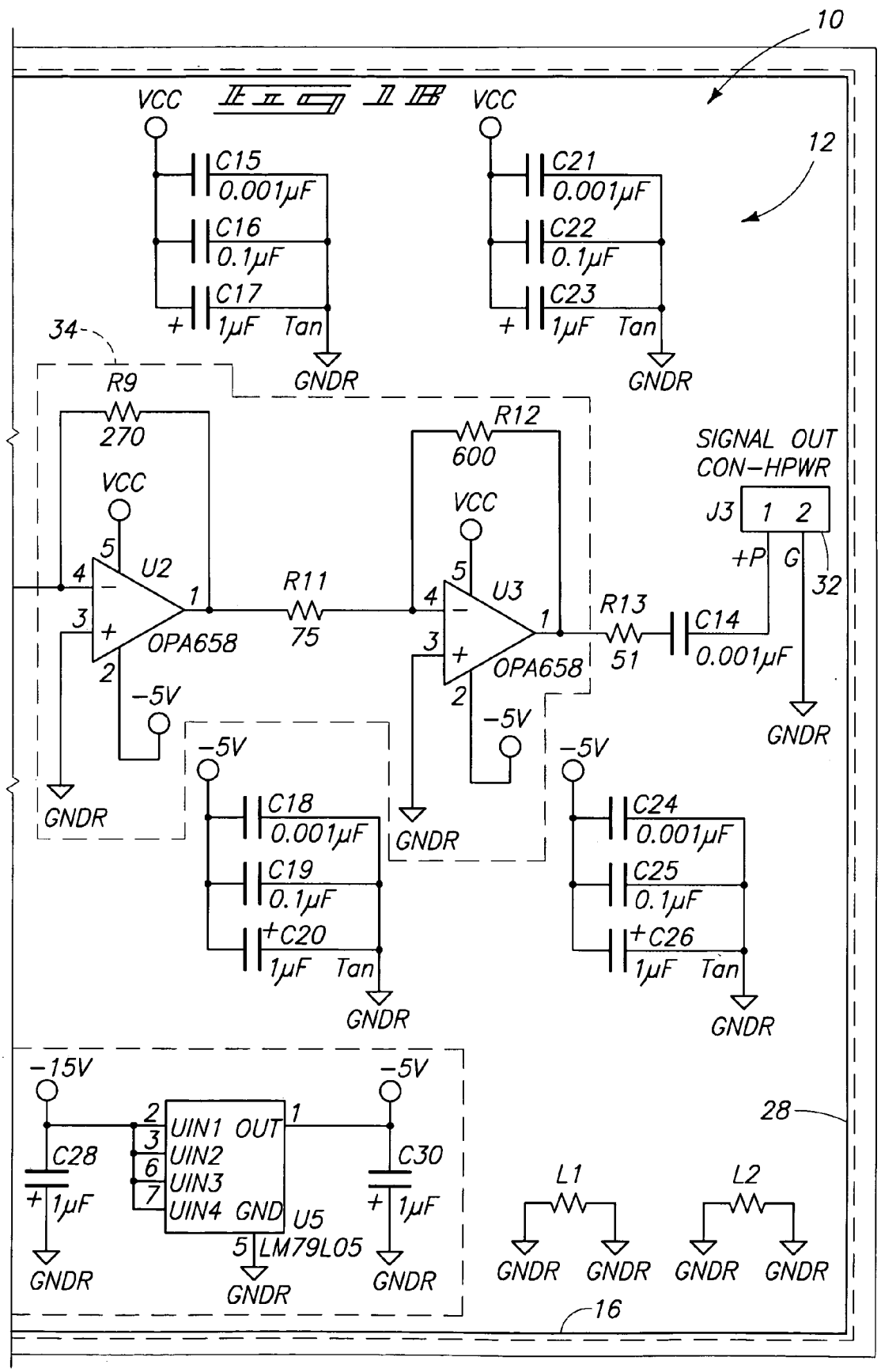

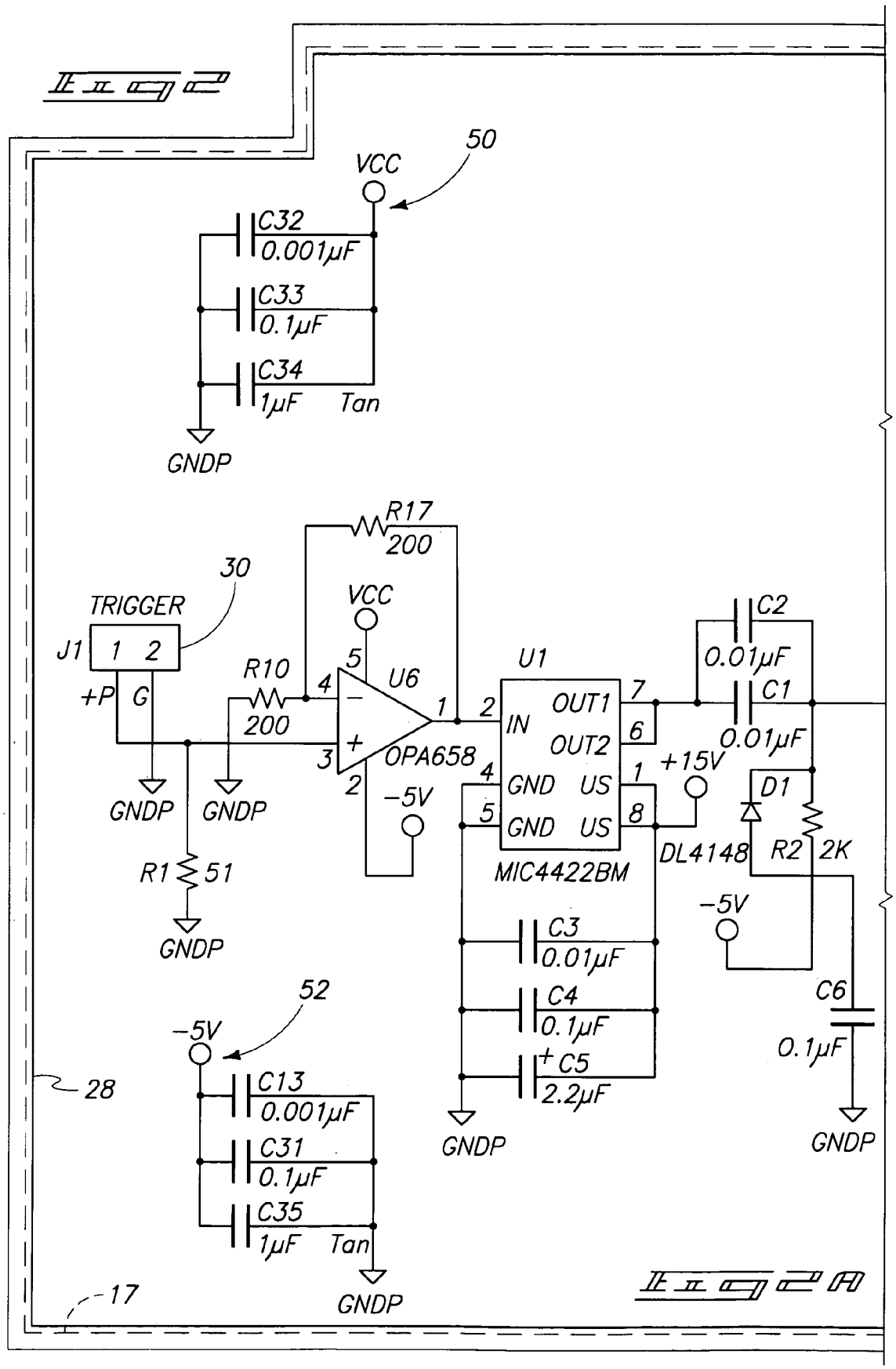

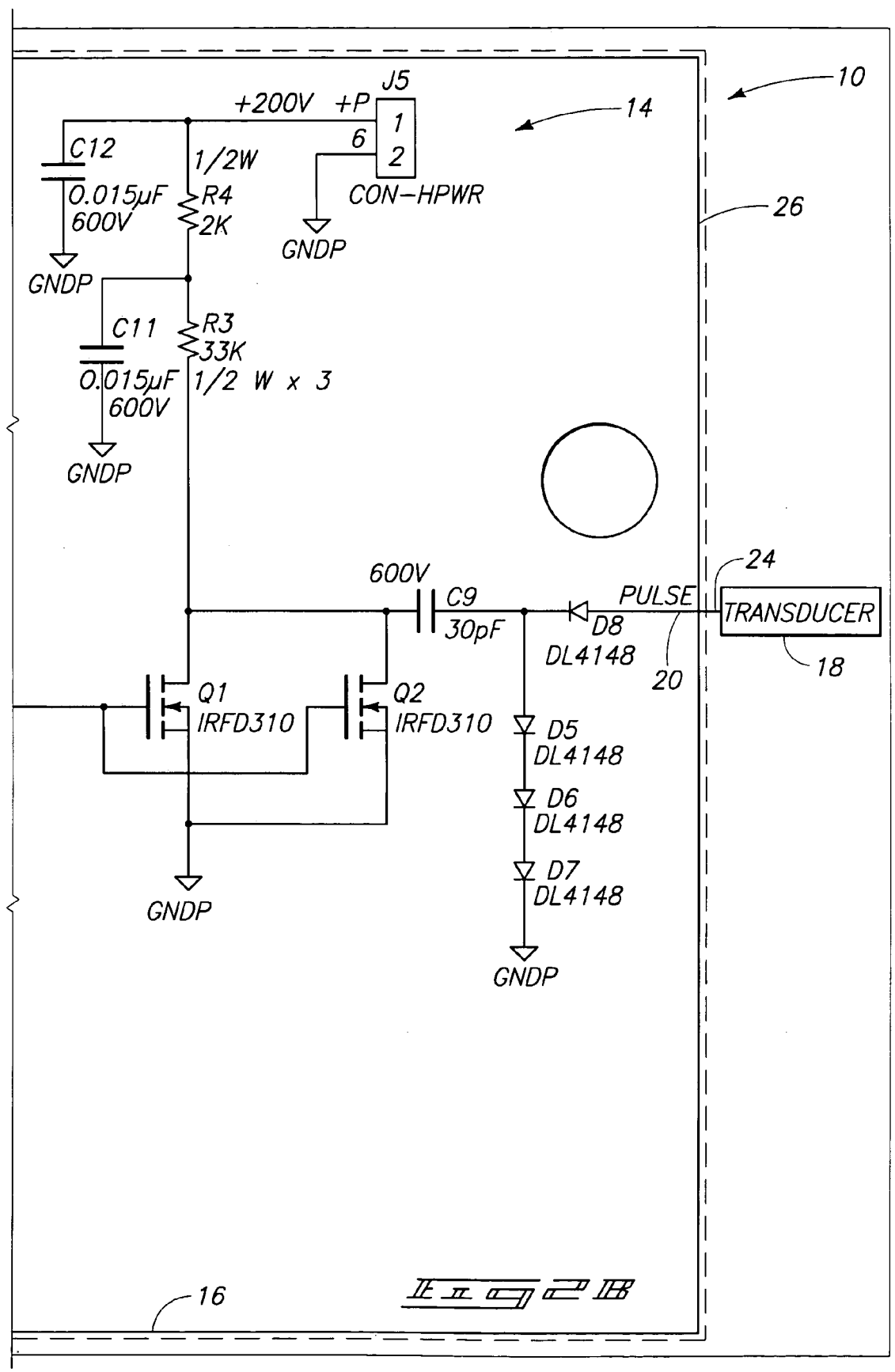

ULTRASONIC PULSER-RECEIVER

GOVERNMENT RIGHTS

This invention was made with Government support under Contract DE-AC07-99ID13727 awarded by the U.S. Department of Energy. The Government has certain rights in the invention.

TECHNICAL FIELD

The invention relates to data acquisition methods and apparatus. Some aspects of the invention relate more particularly to ultrasonic testing methods and apparatus. Some aspects of the invention relate still more particularly to ultrasonic pulser-receivers.

BACKGROUND OF THE INVENTION

Ultrasonic testing equipment is used in a variety of applications such as for measuring flow, determining flaws, measuring thickness, and gauging corrosion. This equipment is used with a variety of materials such as metals, plastics, glass, and chemicals. One particular type of ultrasonic testing apparatus is a pulser-receiver. Pulser-receivers are used for a variety of non-destructive testing applications, including flaw detection and thickness gauging. Some pulser-receivers operate at lower frequencies, such as ½ MHz to 25 MHz. Certain applications require high frequency pulsers-receivers operating at about 100 MHz.

Pulser-receivers are available, for example, from GE-Panametrics, 221 Crescent Street, Waltham, Mass. 02453-3497 USA, such as model number 5058PR, a high voltage pulser-receiver for ultrasonic test and measurement applications requiring a high material penetration capability; model 5072PR, an ultrasonic pulser-receiver configured to provide high energy, high gain performance for low frequency investigation of attenuating materials; model 5073PR, a broadband 75 MHz ultrasonic pulser-receiver which provides flaw detection capabilities for very high frequency, high resolution ultrasonic testing when used with an oscilloscope and appropriate transducers, model 5077PR, an ultrasonic pulser-receiver for providing high voltage square wave performance over a wide range of applications, model 5800PR, a computer-controlled pulser-receiver for general purpose ultrasonic testing using computer-based systems for automatic testing, or stored setups to speed repetitive manual tasks, and model 5900PR, a computer-controlled pulser-receiver for high frequency ultrasonic testing using computer-based systems for automatic testing, or stored setups to speed repetitive manual tasks.

Pulser-receivers are also available from JSR Ultrasonics, A Division of Imagilent, 3800 Monroe Avenue, Pittsford, N.Y. 14534 USA, such as model DPR500, which is a dual channel instrument having two pulser-receivers integrated into one unit, and model DPR300, which is a computer controlled ultrasonic pulser-receiver with a low noise receiver.

For some pulser-receivers, replacement transducers are no longer available. Transducers sometimes fail and require replacement. In some applications, there will be multiple failures per year. The cost of replacement can be, for example, about $10,000 to $16,000. Transducer costs vary based on fabrication yields and availability of parts.

Another problem with existing transducers is that they are physically large, heavy and focused. These attributes require, in some applications, that transducers be servoed to track the front surface of a sample under inspection. To add a servo sub-system to each of the transducers of a system could be very costly.

It would be desirable to have, in some embodiments, lower cost pulser-receivers including lower cost transducers. It would also be desirable to avoid the added cost of the transducer servomechanisms, in some embodiments.

Additionally, the time required for general maintenance (i.e. to replace a failed transducer, align the system, and calibrate the existing transducers) is, for example, 20 to 28 man-days. It would be desirable to provide pulser-receivers, in some embodiments, for which the transducers can be removed and replaced, and the system aligned and calibrated, more quickly.

In computer-controlled pulser-receivers, a computer will typically send a trigger to a pulser-receiver. The pulser-receiver sends out a high voltage pulse in response to the trigger. A piezoelectric transducer converts electrical energy to mechanical energy and sends out a pulse. When the pulse hits a certain material, such as at an interface of different types of materials, a reflection or echo comes back. There will usually be some ringing.

It would desirable to have pulser-receivers with quick recovery times, in some embodiments.

BRIEF DESCRIPTION OF THE DRAWINGS

Preferred embodiments of the invention are described below with reference to the following accompanying drawings.

FIG. 1 is a circuit schematic of receiver circuitry of a pulser-receiver in accordance with various aspects of the invention.

FIG. 2 is a circuit schematic of pulser circuitry of the pulser-receiver.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Some aspects of the invention provide high frequency transducers with depth of field, very near front surface resolution, and high sensitivity.

Some aspects of the invention provide a close coupled pulser-receiver with fast rise and fall time, with gain.

Some aspects of the invention provide a pulser-receiver of relatively small physical size and that allows for a lightweight search head.

Some aspects of the invention provide ultrasonic pulser-receiver circuitry, for use with an ultrasonic transducer, the circuitry comprising a circuit board; ultrasonic pulser circuitry supported by the circuit board and configured to be coupled to an ultrasonic transducer and to cause the ultrasonic transducer to emit an ultrasonic output pulse; receiver circuitry supported by the circuit board, coupled to the pulser circuitry, including protection circuitry configured to protect against the ultrasonic pulse and including amplifier circuitry configured to amplify an echo, received back by the transducer, of the output pulse; and a connector configured to couple the ultrasonic transducer directly to the circuit board, to the pulser circuitry and receiver circuitry, wherein impedance mismatches that would result if the transducer was coupled to the circuit board via a cable can be avoided.

FIGS. 1 and 2 show a pulser-receiver 10 embodying various aspects of the invention. More particularly, FIG. 1 shows receiver circuitry 12 and FIG. 2 shows pulser or transmitter circuitry 14 in accordance with very specific embodiments of the invention. For example, to better enable one of ordinary skill in the art to make and use the invention with undue experimentation, specific component values and integrated circuit part numbers are shown in the figures; however, it will be apparent to those of ordinary skill in the art that similar functionality could be achieved using alternative values or ratios of values or components. The pulser-receiver circuitry is configured to be coupled to a transducer. More particularly, in one embodiment, the pulser-receiver circuitry is configured to be coupled to a model E-1038 ValpeyFisher transducer. Other models could also be used.

The pulser circuitry 14 and receiver circuitry 12 are mounted on a circuit board 16. In some embodiments, the circuit board 16 is a multi-layer circuit board. More particularly, the circuit board 16 has, in some embodiments, five wiring surfaces or planes. These include a top layer or surface (FIG. 1) upon which is mounted the receiver circuitry 12, a bottom layers or surface (FIG. 2) upon which is mounted the pulser circuitry 14, two ground plane layers (not shown) between the top and bottom layers; the first of which is located directly behind the receiver circuitry layer of FIG. 1 and the second of which is located behind the pulser circuitry layer of FIG. 2, and a power rail layer (not shown) centered between the pulser and receiver ground planes.

While other sizes could be used, in some embodiments the circuit board 16 is 0.75"×2.65" resulting in a compact product. The circuit board 16 is, in turn, enclosed within a watertight housing or enclosure 17 with fittings for a cable connector and a transducer.

A transducer 18 is connected to an output 20 of the pulser circuitry 14, and to an input 22 of the receiver circuitry 12 via a common connector 24 (J2) on one end 26 of the circuit board 16. The connector 24 mates with an In/Out connector of the transducer 18. A trigger signal to the pulser circuitry 14 and the output signal from the receiver circuitry 12 are obtained at the opposite end 28 of the circuit board via connectors 30 and 32.

Receiver circuitry 12 shown schematically in FIG. 1 will now be described. The receiver circuitry 12 includes amplifier circuitry 34. More particularly, in the illustrated embodiment, the amplifier circuitry 34 comprises two high-speed current feedback amplifiers, (U-2 and U-3), and their associated feedback resistors. In the illustrated embodiment, amplifiers U-2 and U-3 are defined by OPA658 Burr-Brown integrated circuits; however, other amplifier circuitry could be used, such as circuitry from other manufacturers, other amplifier circuitry designs, or other integrated circuit designations. Feedback resistors R-7, R-8, R-9 are associated with amplifier U-2, and resistors R-11 and R-13 are associated with amplifier U-3.

The receiver circuitry 12 further includes protection circuitry 36 to protect the amplifier circuitry 34 from the pulser circuitry's output pulse. More particularly, in the illustrated embodiment, the protection circuitry 36 includes input shunting diodes D-14 and D-15 that protect the input of U-2 from the pulser circuitry's output pulse but do not conduct for the much smaller transducer output signals generated by the transducer 18 from the received signals.

The receiver circuitry 12 further includes input impedance defining circuitry 37. More particularly, in the illustrated embodiment, the impedance to the receiver circuitry 12 is determined by the sum of the resistance of R-7 and R-8, and equals, in the illustrated embodiment, about 50 Ohms or, more particularly, 52 Ohms in the illustrated embodiment. In some embodiments, a parallel (e.g., 100 Ohm) resistor such as resistor R-6 could be used to define an effective input impedance of 50 Ohms; however, in the illustrated embodiment, resistor R-6 is not loaded or is omitted. The voltage gain of the U-2 amplifier stage is approximately equal to $[-R9/(R7+R8)]=-270/52\approx-5$. This gain is in cascade with the gain of the U-3 stage which is approximately equal to $[-R12/R11]=-630/75\approx-8$. The receiver's total gain (unterminated) is therefore approximately equal to $-5\times-8=40$. For proper operation the output of the receiver circuitry 12 is terminated in 50 Ohms. This termination causes the output of the receiver circuitry 12 to be attenuated by a factor of two, resulting in a terminated gain of approximately twenty for the illustrated embodiment. In the illustrated embodiment, the total receiver bandwidth is at least approximately 100 MHz. More particularly, in the illustrated embodiment, the receiver bandwidth is above 150 MHz and is close to 200 MHz.

Circuitry is included to provide positive and negative voltages for the various circuit elements of the receiver circuitry 12. More particularly, in the illustrated embodiment, voltage regulator circuitry 38 is provided. While other voltages could be used, in the illustrated embodiment, the receiver circuitry 12 receives power from plus and minus five volt rails and the voltage for these rails is generated by plus and minus five volt three terminal regulators U-4 and U-5 respectively. In the illustrated embodiment, the voltage regulator U-4 is defined by an LM78L05 National Semiconductor positive voltage regulator integrated circuit and the voltage regulator U-5 is defined by a LM79L05 negative voltage regulator integrated circuit. These regulators are in turn, powered by +/−15 VDC supplied to the pulser-receiver 10 from an external power supply (e.g., via a connector J4). The power rails are heavily bypassed at each amplifier.

In the illustrated embodiment, the receiver circuitry 12 defines a low noise receiver.

The pulser circuitry 14 is shown schematically in FIG. 2. The pulser circuitry includes an input trigger amplifier U-6 (and associated resistors R17 and R18), a trigger driver U-1, transistors Q-1 and Q-2, discharge capacitor C-7, and associated charging and discharging diodes D-5 through D-8. In the illustrated embodiment, the amplifier U-6 is a Burr-Brown OPA658 op-amp; the trigger driver U-1 is a Micrel MIC4422BM integrated circuit; and transistors Q-1 and Q-2 are International Rectifier IRFD310 power MOSFETs; integrated circuits by other manufacturers and other integrated circuits providing similar functionality are possible. Capacitors C-1 and C-2, diode D-1, resistor R-2, and capacitor C-6 define pulse shaping circuitry for the transistors Q-1 and Q-2. Capacitors C-32, C-33, and C-34 are bypass capacitors that filter the incoming voltage.

The circuitry 14 generates its output pulse through high-speed capacitor discharge. In operation, the circuitry 14 functions as follows:

1. Transistors Q-1 and Q-2 are normally non-conducting which allows capacitor C-7 to charge to approximately 200 VDC through diodes D-5, D-6 and D-7.
2. A trigger pulse received at connector 30 is amplified by U-6 and then applied to the input of the driver U-1.
3. The driver U-1 responds to the trigger by generating a fast positive going large (e.g., 15-volt) pulse at the output of U-1 that is applied to the gates of the transistors Q-1 and Q-2.

4. The gate pulse to Q-1 and Q-2 forces these transistors on at high speed causing C-9 to discharge into the transducer 18 via the diode D-8.

In the illustrated embodiment, the pulse into the transducer is negative going and has amplitude of approximately 200 VDC. Its fall time is <1 nanosecond.

The +/−5 VDC power rails (50 and 52 in FIG. 2) power the amplifier U-6 of the pulser circuitry 14. The driver U-1 is powered from the external +15 VDC supply. The power rails to U-1 and U-6 are heavily bypassed in the same manner as was done for the receiver circuitry.

A high power input or power supply (e.g., 200–300 Volts) is provided to the circuitry 14 via a connector J5. Diode D2, D3, and D4 are protection diodes. Resistors R-3 and R-4 are current limiting resistors for the high power input. Capacitors C-11 and C-12 are bypass capacitors for the high power input and help remove noise and ripple from the high power input.

In some embodiments, some or all of the integrated circuits described above are surface mounted.

Various pulser-receiver embodiments disclosed herein have a fast rise time of less than 5 nanoseconds or, more particularly, of less than 1 nanosecond. Various pulser-receiver embodiments disclosed herein have a front surface ring down of less than 60 nanoseconds or, more particularly, of less than 40 nanoseconds. Various pulser-receiver embodiments disclosed herein have a transducer delay-line of less than 20 microseconds or, more particularly, none is required. Various pulser-receiver embodiments disclosed herein have a focal length of about 19 microseconds or, more particularly, of exactly 19 microseconds. Various pulser-receiver embodiments disclosed herein have a depth of field, in time, of less than +/−32 nanoseconds or, more particularly, of +/−2 microseconds. Various pulser-receiver embodiments disclosed herein have a depth of field, in inches, of less than 0.005 inch or, more particularly, of 0.136 inch.

Applications for the pulser-receiver include, for example, ultrasonic inspection of materials requiring a depth of field and very near surface resolution. Examples include clad measurements, or flaw inspection such as flaw inspection of nuclear fuel, computer chips, wafers, or other materials.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. Ultrasonic pulser-receiver circuitry, for use with an ultrasonic transducer, the circuitry comprising:
    a circuit board;
    ultrasonic pulser circuitry supported by the circuit board and configured to be coupled to an ultrasonic transducer and to cause the ultrasonic transducer to emit an ultrasonic output pulse;
    receiver circuitry supported by the circuit board, coupled to the pulser circuitry, including protection circuitry configured to protect against the ultrasonic pulse and including amplifier circuitry configured to amplify an echo, received back by the transducer, of the output pulse; and
    a connector, proximate an end of the circuit board, configured to couple the ultrasonic transducer directly to the circuit board, to the pulser circuitry and receiver circuitry, wherein impedance mismatches that would result if the transducer was coupled to the circuit board via a cable can be avoided and said ultrasonic pulser-receiver circuitry when in operation having a rise time of less than 5 nanoseconds.

2. Ultrasonic pulser-receiver circuitry in accordance with claim 1 and, when in operation, having a rise time of less than 1 nanosecond.

3. Ultrasonic pulser-receiver circuitry in accordance with claim 1 and, when in operation with an ultrasonic transducer, having a front surface ring down of less than 60 nanoseconds.

4. Ultrasonic pulser-receiver circuitry in accordance with claim 1 and, when in operation with an ultrasonic transducer, having a front surface ring down of less than 40 nanoseconds.

5. Ultrasonic pulser-receiver circuitry in accordance with claim 1 and, when in operation with an ultrasonic transducer, having a transducer delay-line of less than 20 microseconds.

6. Ultrasonic pulser-receiver circuitry in accordance with claim 1 wherein no transducer delay-line is required.

7. Ultrasonic pulser-receiver circuitry in accordance with claim 1 and, when in operation with an ultrasonic transducer, having a focal length of about 19 microseconds.

8. Ultrasonic pulser-receiver circuitry in accordance with claim 1 and, when in operation with an ultrasonic transducer, having a depth of field, in time, of less than +/−32 nanoseconds.

9. Ultrasonic pulser-receiver circuitry in accordance with claim 1 and, when in operation with an ultrasonic transducer, having a depth of field, in time, of less than +/−2 microseconds.

10. Ultrasonic pulser-receiver circuitry in accordance with claim 1 and, when in operation with an ultrasonic transducer, having a depth of field, in inches, of less than 0.005 inch.

11. Ultrasonic pulser-receiver circuitry in accordance with claim 1 and, when in operation with an ultrasonic transducer, having a depth of field, in inches, of less than 0.136 inch.

12. Ultrasonic pulser-receiver circuitry in accordance with claim 1 wherein the circuit board has one side supporting at least a majority of the receiver circuitry and an opposite side supporting at least a majority of the pulser circuitry.

13. Ultrasonic pulser-receiver circuitry in accordance with claim 12 wherein at least a majority of the receiver circuitry is defined by components that are surface mounted onto the circuit board.

14. Ultrasonic pulser-receiver circuitry in accordance with claim 12 wherein at least a majority of the pulser circuitry is defined by components that are surface mounted onto the circuit board.

15. Ultrasonic pulser-receiver circuitry, for use with an ultrasonic transducer, the circuitry comprising:
    a circuit board;
    ultrasonic pulser circuitry supported by the circuit board and configured to be coupled to an ultrasonic transducer and to cause the ultrasonic transducer to emit an ultrasonic output pulse, the pulser circuitry including an input configured to receive an input pulse from an external source, an input trigger amplifier coupled to the input, a trigger driver coupled to the trigger amplifier, a transistor coupled to the trigger amplifier, and circuitry, including a discharge capacitor and charging and discharging diodes, coupled to the transistor;

receiver circuitry supported by the circuit board, coupled to the pulser circuitry, including protection circuitry configured to protect against the ultrasonic pulse and including amplifier circuitry configured to amplify an echo, received back by the transducer, of the output pulse; and a connector configured to couple the ultrasonic transducer directly to the circuit board, to the pulser circuitry and receiver circuitry, wherein impedance mismatches that would result if the transducer was coupled to the circuit board via a cable can be avoided and said ultrasonic pulser-receiver circuitry when in operation having a rise time of less than 5 nanoseconds.

16. Ultrasonic pulser-receiver circuitry in accordance with claim 15 and, when in operation, having a rise time of less than 1 nanosecond.

17. Ultrasonic pulser-receiver circuitry in accordance with claim 15 and, when in operation with an ultrasonic transducer, having a front surface ring down of less than 60 nanoseconds.

18. Ultrasonic pulser-receiver circuitry in accordance with claim 15 and, when in operation with an ultrasonic transducer, having a front surface ring down of less than 40 nanoseconds.

19. Ultrasonic pulser-receiver circuitry in accordance with claim 15 and, when in operation with an ultrasonic transducer, having a transducer delay-line of less than 20 microseconds.

20. Ultrasonic pulser-receiver circuitry in accordance with claim 15 wherein no transducer delay-line is required.

21. Ultrasonic pulser-receiver circuitry in accordance with claim 15 and, when in operation with an ultrasonic transducer, having a focal length of about 19 microseconds.

22. Ultrasonic pulser-receiver circuitry in accordance with claim 15 and, when in operation with an ultrasonic transducer, having a depth of field, in time, of less than +/−32 nanoseconds.

23. Ultrasonic pulser-receiver circuitry in accordance with claim 15 and, when in operation with an ultrasonic transducer, having a depth of field, in time, of less than +/−2 microseconds.

24. Ultrasonic pulser-receiver circuitry in accordance with claim 15 and, when in operation with an ultrasonic transducer, having a depth of field, in inches, of less than 0.005 inch.

25. Ultrasonic pulser-receiver circuitry in accordance with claim 15 and, when in operation with an ultrasonic transducer, having a depth of field, in inches, of less than 0.136 inch.

26. Ultrasonic pulser-receiver circuitry in accordance with claim 15 wherein the circuit board has one side supporting at least a majority of the receiver circuitry and an opposite side supporting at least a majority of the pulser circuitry.

27. Ultrasonic pulser-receiver circuitry in accordance with claim 26 wherein at least a majority of the receiver circuitry is defined by components that are surface mounted onto the circuit board.

28. Ultrasonic pulser-receiver circuitry in accordance with claim 26 wherein at least a majority of the pulser circuitry is defined by components that are surface mounted onto the circuit board.

29. An ultrasonic pulser-receiver comprising:
an ultrasonic transducer;
a circuit board;
ultrasonic pulser circuitry supported by the circuit board and coupled to the ultrasonic transducer to selectively cause the ultrasonic transducer to emit an ultrasonic output pulse, the pulser circuitry including an input configured to receive an input pulse from an external computer, input trigger amplifier circuitry coupled to the input, a trigger driver coupled to the input trigger amplifier circuitry, a high power transistor coupled to the trigger amplifier, and a discharge capacitor and charging and discharging diodes coupled to the transistor; and receiver circuitry supported by the circuit board, coupled to the pulser circuitry, including protection circuitry configured to protect against the ultrasonic pulse and including amplifier circuitry configured to amplify an echo, received back by the transducer, of the output pulse, the ultrasonic pulser-receiver, in operation having a rise time of less than 1 nanosecond.

30. An ultrasonic pulser-receiver in accordance with claim 29 and having, in operation, a front surface ring down of less than 60 nanoseconds.

31. An ultrasonic pulser-receiver in accordance with claim 29 and having, in operation, a front surface ring down of less than 40 nanoseconds.

32. An ultrasonic pulser-receiver in accordance with claim 30 and having, in operation, a transducer delay-line of less than 20 microseconds.

33. An ultrasonic pulser-receiver in accordance with claim 31 wherein no transducer delay-line is required.

34. An ultrasonic pulser-receiver in accordance with claim 32 and, in operation, having a focal length of about 19 microseconds.

35. An ultrasonic pulser-receiver in accordance with claim 33 and, in operation, having a depth of field, in time, of less than +/−32 nanoseconds.

36. An ultrasonic pulser-receiver in accordance with claim 34 and, in operation, having a depth of field, in time, of less than +/−2 microseconds.

37. An ultrasonic pulser-receiver in accordance with claim 35 and, in operation, having a depth of field, in inches, of less than 0.005 inch.

38. An ultrasonic pulser-receiver in accordance with claim 36 and, in operation, having a depth of field, in inches, of less than 0.136 inch.

39. An ultrasonic pulser-receiver in accordance with claim 38 wherein the circuit board has one side supporting at least a majority of the receiver circuitry and an opposite side supporting at least a majority of the pulser circuitry.

40. An ultrasonic pulser-receiver in accordance with claim 39 wherein at least a majority of the receiver circuitry is defined by components that are surface mounted onto the circuit board.

41. An ultrasonic pulser-receiver in accordance with claim 40 wherein at least a majority of the pulser circuitry is defined by components that are surface mounted onto the circuit board.

42. An ultrasonic pulser-receiver comprising:
an ultrasonic transducer;
a circuit board;
ultrasonic pulser circuitry supported by the circuit board and coupled to the ultrasonic transducer to selectively cause the ultrasonic transducer to emit an ultrasonic output pulse, the pulser circuitry including an input configured to receive an input pulse from an external computer, input trigger amplifier circuitry coupled to the input, a trigger driver coupled to the input trigger amplifier circuitry, a high power transistor coupled to the trigger amplifier, and a discharge capacitor and charging and discharging diodes coupled to the transistor;

receiver circuitry supported by the circuit board, coupled to the pulser circuitry, including protection circuitry configured to protect against the ultrasonic pulse and including amplifier circuitry configured to amplify an echo, received back by the transducer, of the output pulse;

a connector, proximate an end of the circuit board, configured to couple the ultrasonic transducer directly to the circuit board, to the pulser circuitry and to the receiver circuitry; and a housing surrounding the circuit board and protecting the circuit board against water, after the transducer has been coupled to the connector;

the ultrasonic pulser-receiver having, in operation, a rise time of less than 1 nanosecond;

the ultrasonic pulser-receiver having, in operation, a front surface ring down of less than 60 nanoseconds;

the ultrasonic pulser-receiver having, in operation, a transducer delay-line of less than 20 microseconds; and the ultrasonic pulser-receiver having, in operation, a depth of field, in inches, of less than 0.136 inch.

* * * * *